(12) United States Patent
Gao

(10) Patent No.: US 10,942,495 B2
(45) Date of Patent: Mar. 9, 2021

(54) MOVEMENT CONTROLLER OF SCANNING BED IN MEDICAL APPARATUS

(71) Applicant: Beijing Neusoft Medical Equipment Co., Ltd., Beijing (CN)

(72) Inventor: Shang Gao, Beijing (CN)

(73) Assignee: Beijing Neusoft Medical Equipment Co., Ltd., Beijing (CN)

( * ) Notice: Subject to any disclaimer, the term of this patent is extended or adjusted under 35 U.S.C. 154(b) by 0 days.

(21) Appl. No.: 15/990,245

(22) Filed: May 25, 2018

(65) Prior Publication Data

US 2018/0341240 A1 Nov. 29, 2018

(30) Foreign Application Priority Data

May 25, 2017 (CN) .......................... 201710378211.2

(51) Int. Cl.
  *G05B 19/042* (2006.01)
  *A61G 7/018* (2006.01)
  (Continued)

(52) U.S. Cl.
  CPC .............. *G05B 19/042* (2013.01); *A61B 6/04* (2013.01); *A61G 7/005* (2013.01); *A61G 7/008* (2013.01);
  (Continued)

(58) Field of Classification Search
  CPC .... A61G 7/018; A61G 2203/32; A61G 7/015; A61G 2203/44; A61G 7/005;
  (Continued)

(56) References Cited

U.S. PATENT DOCUMENTS 3,394,264 A * 7/1968 Busey .................. G01P 3/4802
  250/233
3,890,837 A * 6/1975 Frizzell .................. G01F 1/125
  73/861.77

(Continued)

FOREIGN PATENT DOCUMENTS

CN 2819305 Y 9/2006
CN 200995031 Y 12/2007
(Continued)

OTHER PUBLICATIONS

State Intellectual Property Office of the People's Republic of China, Office Action and Search Report Issued in Application No. 201710378211.2, dated Jan. 11, 2019, 16 pages. (Submitted with Partial Translation).

(Continued)

*Primary Examiner* — Darrin D Dunn
(74) *Attorney, Agent, or Firm* — McCoy Russell LLP

(57) ABSTRACT

A controlling apparatus is provided. According to an example, the controlling apparatus comprises: an operating body configured to bear acting forces; a mechanical sensing apparatus arranged on a surface of the operating body and configured to sense the acting forces and convert the acting forces into electric signals; and a controlling module configured to determine a resultant force of the acting forces according to the electric signals and control a controlled object to move along a direction of the resultant force of the acting forces.

16 Claims, 10 Drawing Sheets

(51) Int. Cl.
*A61B 6/04* (2006.01)
*A61G 13/04* (2006.01)
*A61G 7/008* (2006.01)
*A61G 7/005* (2006.01)

(52) U.S. Cl.
CPC .............. *A61G 7/018* (2013.01); *A61G 13/04* (2013.01); *A61G 2203/32* (2013.01); *A61G 2203/34* (2013.01); *G05B 2219/21004* (2013.01); *G05B 2219/37357* (2013.01)

(58) Field of Classification Search
CPC ................ A61G 7/012; A61G 2203/30; A61G 2203/74; A61G 7/00; A61G 7/057; A61G 2203/10; A61G 2203/38; A61G 2203/72; A61G 2203/726; A61B 5/1115; A61B 5/6892; A61B 5/447; A61B 2562/0252; A61B 2562/046; A61B 5/002; A61B 2562/0219; A61B 5/1036; A61B 5/11; A61B 5/1116
See application file for complete search history.

(56) References Cited

U.S. PATENT DOCUMENTS

| | | | | |
|---|---|---|---|---|
| 4,814,661 A * | 3/1989 | Ratzlaff | ............... | A01L 11/00 310/319 |
| 4,843,308 A * | 6/1989 | Frame | ............... | A01L 11/00 310/338 |
| 5,253,656 A * | 10/1993 | Rincoe | ............... | A61B 5/1036 600/595 |
| 6,094,760 A * | 8/2000 | Nonaka | ............... | A61B 6/0457 5/600 |
| 6,260,805 B1 * | 7/2001 | Yocum, Jr. | ............... | B64G 1/26 244/164 |
| 7,656,299 B2 * | 2/2010 | Gentry | ............... | A61B 5/1113 340/562 |
| 7,962,981 B2 * | 6/2011 | Lemire | ............... | A61G 7/005 5/616 |
| 8,031,094 B2 * | 10/2011 | Hotelling | ............... | H03M 3/494 341/143 |
| 8,085,252 B1 * | 12/2011 | Lee | ............... | G06F 3/044 345/174 |
| 8,606,344 B2 * | 12/2013 | DiMaio | ............... | A61B 5/704 600/407 |
| 8,766,925 B2 * | 7/2014 | Perlin | ............... | G06F 3/0233 345/173 |
| 8,850,640 B2 * | 10/2014 | Buettner | ............... | A61B 6/0457 5/601 |
| 8,909,378 B2 * | 12/2014 | Rawls-Meehan | ............... | A47C 20/041 5/616 |
| 9,383,251 B2 * | 7/2016 | Dixon | ............... | A61B 5/1115 |
| 9,778,635 B2 * | 10/2017 | Cudak | ............... | G05B 15/02 |
| 10,268,181 B1 * | 4/2019 | Nevins | ............... | G09B 5/067 |
| 10,278,512 B2 * | 5/2019 | Stjerna | ............... | A47C 23/0435 |
| 2006/0260054 A1 * | 11/2006 | Lubbers | ............... | A61G 7/018 5/621 |
| 2009/0143703 A1 * | 6/2009 | Dixon | ............... | A61B 5/1115 600/587 |
| 2010/0245246 A1 * | 9/2010 | Rosenfeld | ............... | G06F 3/0414 345/163 |
| 2011/0050569 A1 * | 3/2011 | Marvit | ............... | G06F 3/017 345/158 |
| 2011/0066287 A1 * | 3/2011 | Flanagan | ............... | A61G 7/018 700/275 |
| 2011/0231996 A1 * | 9/2011 | Lemire | ............... | A61G 7/005 5/613 |
| 2011/0239370 A1 * | 10/2011 | Turo | ............... | A61B 5/447 5/600 |
| 2012/0038484 A1 * | 2/2012 | Dixon | ............... | A61B 5/1115 340/666 |
| 2012/0169612 A1 * | 7/2012 | Alameh | ............... | G06F 3/0338 345/173 |
| 2012/0317713 A1 * | 12/2012 | Eytan | ............... | A61G 7/1026 5/81.1 R |
| 2013/0015596 A1 * | 1/2013 | Mozeika | ............... | B25J 9/0084 264/40.1 |
| 2013/0152308 A1 * | 6/2013 | Valdemoros Tobia | ... | A61B 5/11 5/611 |
| 2013/0205501 A1 * | 8/2013 | Robertson | ............... | A61G 7/018 5/611 |
| 2013/0281804 A1 * | 10/2013 | Lee | ............... | A61B 5/447 600/324 |
| 2013/0317393 A1 * | 11/2013 | Weiss | ............... | G06F 19/3418 600/587 |
| 2014/0026327 A1 * | 1/2014 | Taylor | ............... | A47C 27/082 5/713 |
| 2014/0039351 A1 * | 2/2014 | Mix | ............... | A61B 5/1114 600/587 |
| 2014/0066815 A1 * | 3/2014 | Williamson | ............... | A61B 5/6892 600/595 |
| 2014/0252684 A1 * | 9/2014 | Swanson | ............... | B29C 67/0055 264/401 |
| 2015/0128352 A1 * | 5/2015 | Papaioannou | ............... | A61G 7/0573 5/699 |
| 2015/0130586 A1 * | 5/2015 | Rawls-Meehan | ............... | A47C 20/041 340/4.4 |
| 2015/0164238 A1 * | 6/2015 | Benson | ............... | G16H 50/30 340/540 |
| 2015/0173667 A1 * | 6/2015 | Ben Shalom | ............... | A61G 5/1043 702/139 |
| 2015/0242028 A1 * | 8/2015 | Roberts | ............... | G06F 3/044 345/173 |
| 2015/0351982 A1 * | 12/2015 | Krenik | ............... | A47C 23/06 5/616 |
| 2016/0015183 A1 * | 1/2016 | Stjerna | ............... | A47C 23/0435 5/727 |
| 2016/0022218 A1 * | 1/2016 | Hayes | ............... | A61G 7/005 600/301 |
| 2016/0100696 A1 * | 4/2016 | Palashewski | ............... | A47C 31/00 700/90 |
| 2016/0128610 A1 * | 5/2016 | Kostic | ............... | A61B 5/1115 5/613 |
| 2016/0166178 A1 * | 6/2016 | Fuss | ............... | A61B 5/1038 600/592 |
| 2016/0166453 A1 * | 6/2016 | Furman | ............... | A61G 7/018 700/275 |
| 2016/0167310 A1 * | 6/2016 | Lee | ............... | B29C 67/0088 700/98 |
| 2016/0209819 A1 * | 7/2016 | Cudak | ............... | G05B 15/02 |
| 2016/0287459 A1 * | 10/2016 | Lemire | ............... | A61G 7/005 |
| 2016/0367042 A1 * | 12/2016 | Fisher | ............... | A47C 7/18 |
| 2016/0367170 A1 * | 12/2016 | Larson | ............... | G16H 20/10 |
| 2017/0020413 A1 * | 1/2017 | Otaka | ............... | A61B 5/11 |
| 2017/0127847 A1 * | 5/2017 | Rawls-Meehan | ............... | A47C 7/027 |
| 2017/0128297 A1 * | 5/2017 | Cernasov | ............... | A61G 7/0573 |
| 2017/0215826 A1 * | 8/2017 | Johnson | ............... | A61B 6/56 |
| 2017/0224565 A1 * | 8/2017 | Lachenbruch | ............... | A61G 7/001 |
| 2017/0246062 A1 * | 8/2017 | O'Keefe | ............... | A61G 7/002 |
| 2017/0325683 A1 * | 11/2017 | Larson | ............... | G16H 50/30 |
| 2017/0329403 A1 * | 11/2017 | Lai | ............... | G06F 3/014 |
| 2018/0024517 A1 * | 1/2018 | Halperin | ............... | G05B 19/4099 700/98 |
| 2018/0089979 A1 * | 3/2018 | Wiggermann | ............... | G08B 21/0446 |
| 2018/0093417 A1 * | 4/2018 | Yaw | ............... | B29C 64/393 |
| 2018/0185221 A1 * | 7/2018 | Hayes | ............... | A61G 7/018 |
| 2018/0297113 A1 * | 10/2018 | Preston | ............... | B22F 3/008 |
| 2019/0009472 A1 * | 1/2019 | Mark | ............... | B29C 70/384 |
| 2019/0118260 A1 * | 4/2019 | Schmitt | ............... | B33Y 30/00 |
| 2019/0150865 A1 * | 5/2019 | Johnson | ............... | A61B 6/4405 |

FOREIGN PATENT DOCUMENTS

| | | |
|---|---|---|
| CN | 201594225 U | 9/2010 |
| CN | 102236336 A | 11/2011 |
| CN | 103218905 A | 7/2013 |
| CN | 103446707 A | 12/2013 |
| CN | 104793740 A | 7/2015 |
| CN | 204502376 U | 7/2015 |
| CN | 105064869 A | 11/2015 |

(56) References Cited

FOREIGN PATENT DOCUMENTS

| | | |
|---|---|---|
| CN | 106094811 A | 11/2016 |
| CN | 106598156 A | 4/2017 |
| WO | 2015058390 A1 | 4/2015 |

OTHER PUBLICATIONS

State Intellectual Property Office of the People's Republic of China, Office Action and Search Report Issued in Application No. 201710378211.2, dated Jun. 20, 2019, 19 pages. (Submitted with Partial Translation).

* cited by examiner

MOVEMENT CONTROLLER OF SCANNING BED IN MEDICAL APPARATUS

CROSS REFERENCE TO RELATED APPLICATIONS

This application claims priority to Chinese Patent Application No. 201710378211.2 filed on May 25, 2017, the entire content of which is incorporated herein by reference in its entirety for all purposes.

TECHNICAL FIELD

The present disclosure relates to a controlling apparatus.

BACKGROUND

With the continuous development of automatic control technology, controlling apparatuses are used in more and more fields to control the movement of a controlled object, thereby relieving the workload of people. For example, in a machining field, requirements for a lathe for producing and processing parts, such as requirements for location, height or direction of the lathe may be different at different stages during part production and processing, thus, the requirements may be met by controlling movement of the lathe with a lathe controller. In general, a controlling apparatus may include a plurality of function buttons, each of which is used to control a controlled object to perform a movement corresponding to the function button. For example, the controlled object may ascend when an ascending button is operated and descend when a descending button is operated.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS's products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during CT scanning process.

DETAILED DESCRIPTION

Figure 1:
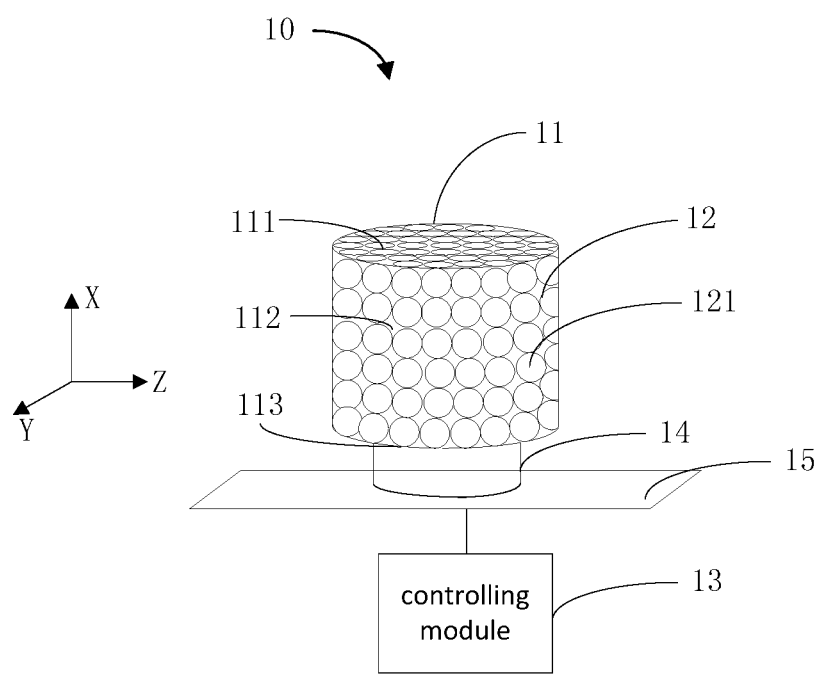
FIG. 1 is a schematic diagram illustrating a controlling apparatus according to an example of the present disclosure.

FIG. 1 is a schematic diagram illustrating a controlling apparatus 10 according to an example of the present disclosure. The controlling apparatus 10 may be a movement controller of a scanning bed in a medical instrument field. The movement controller may be used to control the scanning bed to perform different movements, such as one or more of rotation, tilt, sway, translation, ascent, descent, etc. Generally, the scanning bed will perform a corresponding movement when an operator operates the movement controller and stop moving when the operator stops operating the movement controller. The controlling apparatus 10 shown in FIG. 1 may include: an operating body 11, a mechanical sensing apparatus 12, a controlling module 13, a fixing apparatus 14, and a fixing base 15.

The operating body 11 may be provided with the mechanical sensing apparatus 12 on a surface of the operating body 11 and the mechanical sensing apparatus 12 may be configured to bear different acting forces and convert the acting forces to electric signals. In an example, the operating body 11 may be arranged on the fixing base 15 through the fixing apparatus 14 such that the operating body 11 may only rotate while keeping stationary in other directions.

The mechanical sensing apparatus 12 may be configured to sense acting forces applied on the operating body 11. The mechanical sensing apparatus 12 may include a plurality of stress sensors 121 which may be arranged on the surface of the operating body 11. Further, the plurality of stress sensors 121 may be arranged on an upper surface 111, a side surface 112 and a lower surface 113 of the operating body 11. In an example, the plurality of stress sensors 121 may be uniformly distributed on the upper surface 111, the side surface 112 and the lower surface 113 of the operating body 11. The plurality of stress sensors 121 may convert acting forces applied to respective positions of the stress sensors to electric signals and transmit the electric signals to the controlling module 13.

Figure 2:
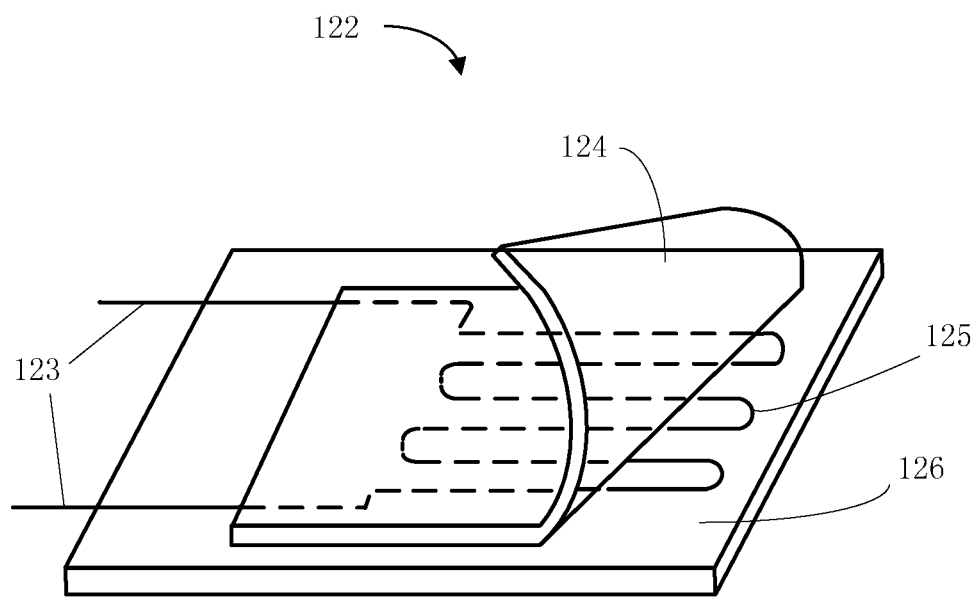
FIG. 2 is a schematic diagram illustrating a structure of a sensing element in a controlling apparatus according to an example of the present disclosure.

In an example, each stress sensor 121 may include a sensing element 122. As shown in FIG. 2, the sensing element 122 may include two leads 123, a cover layer 124, a resistance grid 125, a substrate 126, and the like. The resistance grid 125 may be fixed on the substrate 126 through an adhesive. The two leads 123 are respectively connected with two output terminals of the resistance grid 125 so as to transmit out an electric signal from the resistance grid 125. The cover layer 124 covering the resistance grid 125 may be used to protect the resistance grid 125.

When the stress sensor 121 is deformed due to an acting force, the resistance grid 125 in the sensing element 122 inside the stress sensor 121 may suffer a strain, which further leads to a change in the resistance of the resistance grid 125, thereby generating an electric signal corresponding to the acting force. In an example, the resistance grid 125 may be formed by curving a resistance wire with a high resistance coefficient. The resistance wire with a high resistance coefficient may be 0.01 mm-0.05 mm in diameter. Because of high sensitivity of the resistance wire with a high resistance coefficient, a stress sensor made of the resistance wire may sense a change of an acting force relatively accurately, thereby obtaining a relatively accurate electric signal.

The controlling module 13 may be configured to receive electric signals from the mechanical sensing apparatus 12 and determine a resultant force of acting forces according to the electric signals. In an example, the controlling module 13 may determine a magnitude and a direction of the resultant force of the acting forces according to the electric signals and control a controlled object 41 to move along the direction of the resultant force of the acting forces at a corresponding speed according to the magnitude and the direction of the resultant force of the acting forces. The moving speed of the controlled object 41 may be determined according to the magnitude of the resultant force of the acting forces. In an example, the moving speed of the controlled object 41 is positively related to the magnitude of the resultant force of the acting forces.

Figure 3:
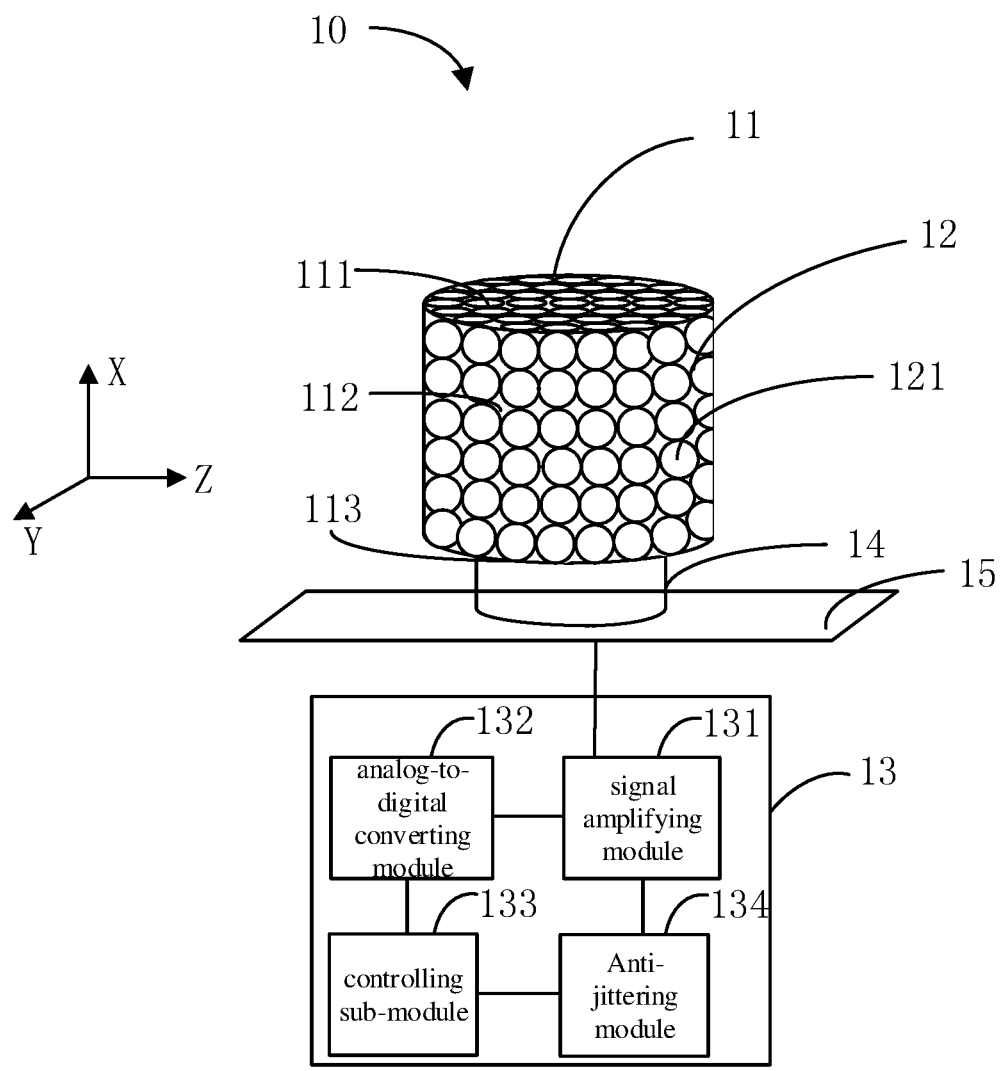
FIG. 3 is a schematic diagram illustrating a controlling apparatus according to another example of the present disclosure.

FIG. 3 is a schematic diagram illustrating a controlling apparatus according to another example of the present disclosure. In an example, referring to FIG. 3, the controlling module 13 may include a signal amplifying module 131, an analog-to-digital converting module 132 and a controlling sub-module 133. The signal amplifying module 131 may be configured to receive electric signals from the mechanical sensing apparatus 12 and amplify the electric signals to generate amplified electric signals. The analog-to-digital converting module 132 may be configured to convert the amplified electric signals into digital signals. Then, the controlling sub-module 133 may be configured to determine a resultant force of acting forces (including a magnitude and a direction of the resultant force of the acting forces) based on the digital signals and then control the controlled object 41 to move according to the resultant force of the acting forces such that the controlled object 41 moves along the direction of the resultant force of the acting forces. In addition, the moving speed of the controlled object 41 may be determined according to the magnitude of the resultant force of the acting forces.

In an example, the controlling module 13 may further include an anti-jittering module 134. The anti-jittering 134 module may be configured to perform anti-jittering processing on electric signals that are converted and output by the mechanical sensing apparatus 12 based on acting forces so as to reserve electric signals converted based on effective ones of the acting forces. Accordingly, the controlling module 13 may be configured to control the controlled object 41 to move along a direction of a resultant force of the effective ones of the acting forces according to the electric signals converted based on the effective ones of the acting forces. The moving speed of the controlled object 41 may be determined according to a magnitude of the resultant force of the effective ones of the acting forces.

It should be noted that the anti-jittering module 134 may be specifically configured to filter out an interference signal in the electric signals to avoid movement of the controlled object 41 caused by a corresponding interferential acting force. For example, when an operator touches the controlling apparatus 10 by accident, an electric signal converted from an acting force of touching the controlling apparatus 10 may be filtered out by the anti-jittering module 134, thereby preventing the controlled object 41 from moving suddenly due to the accidental touch on the controlling apparatus 10 by the operator. In another example, the anti-jittering module 134 may further be configured to perform an anti-jittering processing on the amplified electric signals and output the amplified electric signals subjected to the anti-jittering processing to the analog-to-digital converting module 132. In an example, the anti-jittering processing may be performed in a manner of filtering. For example, the anti-jittering module 134 may collect electric signals over a particular time interval (e.g. 1 ms, 3 ms, etc.) and then perform an anti-jittering processing on the collected electric signals so as to obtain electric signals corresponding to effective ones of acting forces, where the time interval may be set based on experience or a practical application, which is not specifically limited herein. When the anti-jittering processing is performed in a manner of filtering, a filtering algorithm such as a de-jittering filtering algorithm, an amplitude-limiting filtering algorithm, a median filtering algorithm or an arithmetic mean filtering algorithm may be adopted, and no specific limitations are made to the adopted filtering algorithm. In some examples, additionally or alternatively, the anti-jittering processing comprises performing filtering and denoising of the electric signals.

Further, the controlling apparatus 10 may further include a driving apparatus configured to drive the controlled object 41 to perform a corresponding movement. Generally, the controlling module 13 may control the driving apparatus to drive the controlled object 41 to move according to a resultant force of acting forces.

Figure 4:
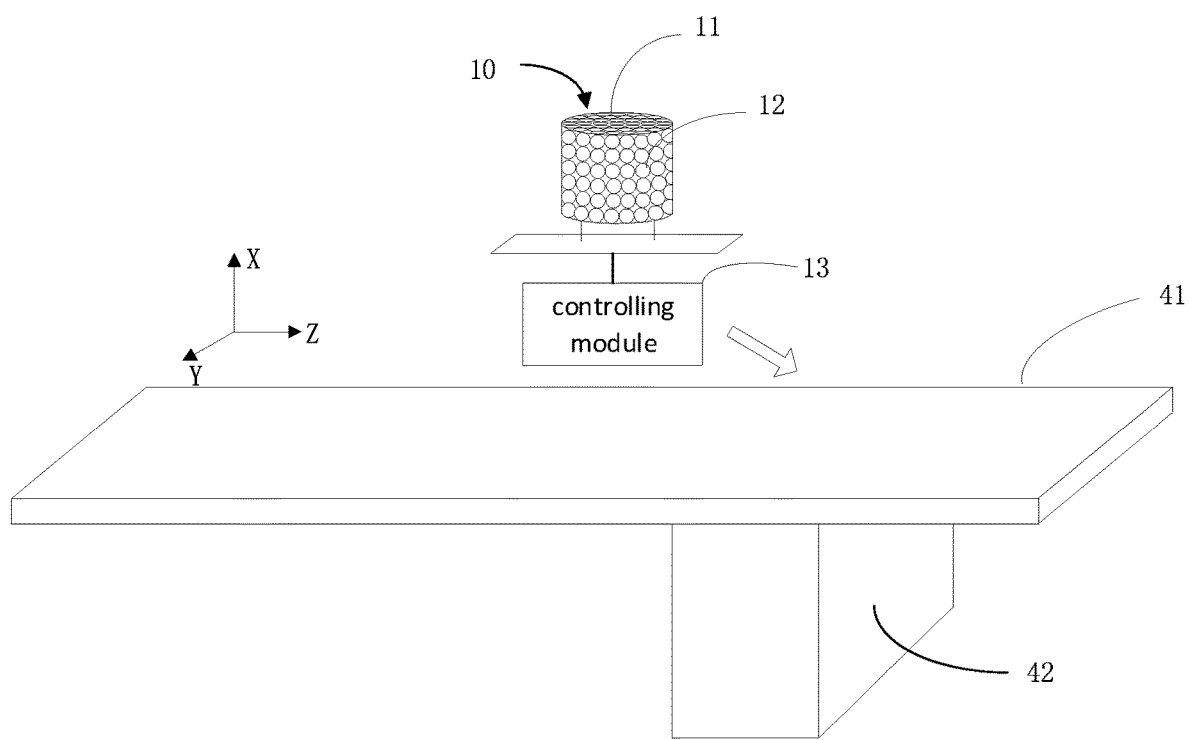
FIG. 4 is a schematic diagram illustrating an application scenario of a controlling apparatus according to an example of the present disclosure.

FIG. 4 is a schematic diagram illustrating an application scenario of a controlling apparatus according to an example of the present disclosure. The controlling apparatus 10, the controlled object 41 and a supporting apparatus 42 may be included in the application scenario shown in FIG. 4. The supporting apparatus 42 may be an apparatus independent of the controlled object 41 or may be a part of the controlled object 41. In an example, the controlled object 41 may be a scanning bed in a medical device. The scanning bed may perform various types of movements. Correspondingly, the controlling apparatus 10 may be a movement controller for controlling the movement of the scanning bed. The controlling apparatus 10 may control the scanning bed to perform various types of movements such as one or more of rotation, tilt, sway, translation, ascent and descent through a driving apparatus. As shown in FIG. 4, the controlled object 41 has a long side parallel to a Z-axis, a short side parallel to a Y-axis and an upper surface vertical to an X-axis. To depict how the controlling apparatus 10 controls the movement of the controlled object 41 more clearly and plainly, a detailed description will be made in conjunction with FIG. 5-FIG. 11.

Figure 5:
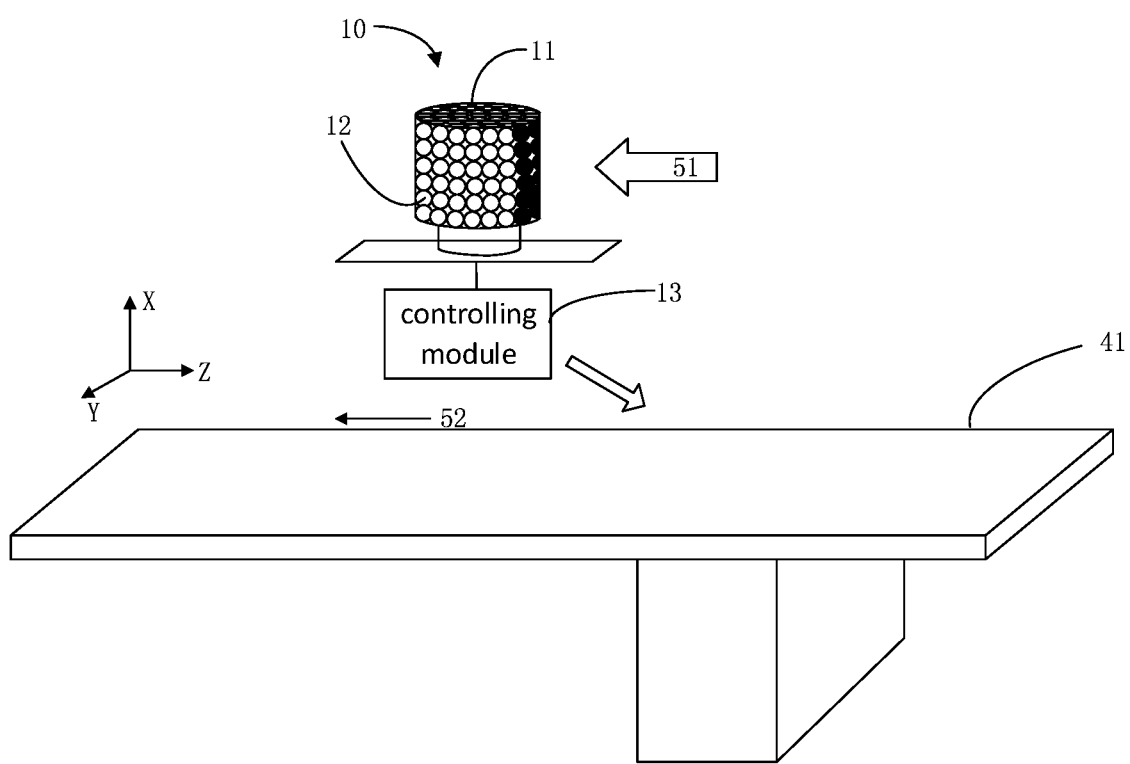
FIG. 5 is a schematic diagram illustrating that a controlling apparatus controls a controlled object to translate according to an example of the present disclosure.

FIG. 5 is a schematic diagram illustrating that the controlling apparatus 10 controls the controlled object 41 to translate according to an example of the present disclosure. Translation of the controlled object 41 may refer to the controlled object 41 performing a movement parallel to a Y-Z plane, for example, the controlled object 40 moves along a negative direction of the Z-axis, as shown in FIG. 5. Moreover, the translation of the controlled object 41 may further include a movement of the controlled object 41 along a positive direction of the Z-axis, a movement of the controlled object 41 along a positive direction of the Y-axis, a movement of the controlled object 41 along a negative direction of the Y-axis, and a movement of the controlled object 41 in the current plane along a direction forming an inclined angle with the Z-axis or Y-axis.

In the example shown in FIG. 5, when the side surface 112 of the operating body 11 bears an acting force 51 applied along the negative direction of the Z-axis, at least one stress sensor 121 of the mechanical sensing apparatus 12 (e.g. the black stress sensors 121 shown in FIG. 5) arranged on the side surface 112 may sense part of the acting force 51, convert respective part of the acting force 51 sensed into electric signals, and send the electric signals to the controlling module 13. The controlling module 13 may determine a magnitude and a direction of a resultant force of respective parts of the acting force 51 sensed by the at least one stress sensor 121 according to the electric signals. The direction of the resultant force of respective parts of the acting force 51 sensed by the at least one stress sensor 121 may be determined as the negative direction of the Z-axis so that the controlled object 41 is controlled to translate along the negative direction of the Z-axis (i.e. a direction indicated by the arrow 52 shown in FIG. 5). Further, the moving speed of the controlled object 41 may be determined according to the magnitude of the resultant force of respective parts of the acting force 51 sensed by the at least one stress sensor 121.

It should be noted that the stress sensors 121 on the side surface 112 of the operating body 11 shown in FIG. 5 are black, which indicates that the stress sensors 121 sense an acting force. Likewise, the controlling apparatus 10 may control the controlled object 41 to translate along another direction in the Y-Z plane based on the same principle as shown in FIG. 5 for translation. For example, when the controlled object 41 is to translate along the positive direction of the Y-axis, a pushing force along the positive direction of the Y-axis may be applied to the operating body 11.

Figure 6:
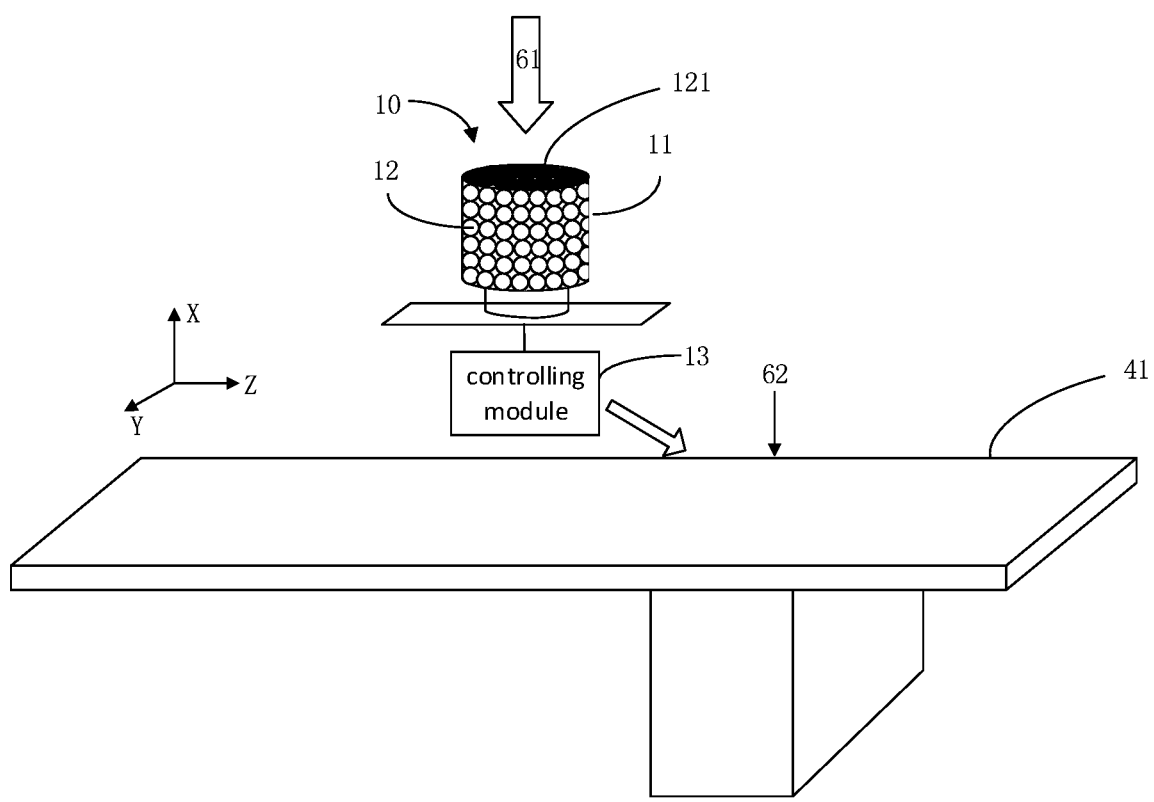
FIG. 6 is a schematic diagram illustrating that a controlling apparatus controls a controlled object to descend according to an example of the present disclosure.

FIG. 6 is a schematic diagram illustrating that the controlling apparatus 10 controls the controlled object 41 to descend according to an example of the present disclosure. Descent of the controlled object 41 may refer to the controlled object moving along the negative direction of the X-axis. As shown in FIG. 6, when the upper surface 111 of the operating body 11 bears an acting force 61 along the negative direction of the X-axis, at least one stress sensor 121 of the mechanical sensing apparatus 12 (e.g. the black stress sensors 121 shown in FIG. 6) arranged on the upper surface 111 may sense part of the acting force 61, convert respective part of the acting force 61 sensed into electric signals, and send the electric signals to the controlling module 13. The controlling module 13 may determine a magnitude and a direction of a resultant force of respective parts of the acting force 61 sensed by the at least one stress sensor 121 according to the electric signals. The direction of the resultant force of respective parts of the acting force 61 sensed by the at least one stress sensor 121 may be determined as the negative direction of the X-axis so that the controlled object 41 is controlled to move along the negative direction of the X-axis (i.e. a direction indicated by the arrow 62 shown in FIG. 6). Besides, the moving speed of the controlled object 41 may be determined according to the magnitude of the resultant force of respective parts of the acting force 61 sensed by the at least one stress sensor 121.

It should be noted that the stress sensors 121 on the upper surface 111 of the operating body 11 shown in FIG. 6 are black, which indicates that the stress sensors 121 sense an acting force. Similarly, as shown in FIG. 6, the controlling apparatus 10 may control the controlled object 41 to move along the positive direction of the X-axis with a difference being that an acting force along the positive direction of the X-axis is to be applied on the operating body 11, for example, an acting force along the positive direction of the X-axis may be applied to the lower surface 113 of the operating body 11.

Figure 7:
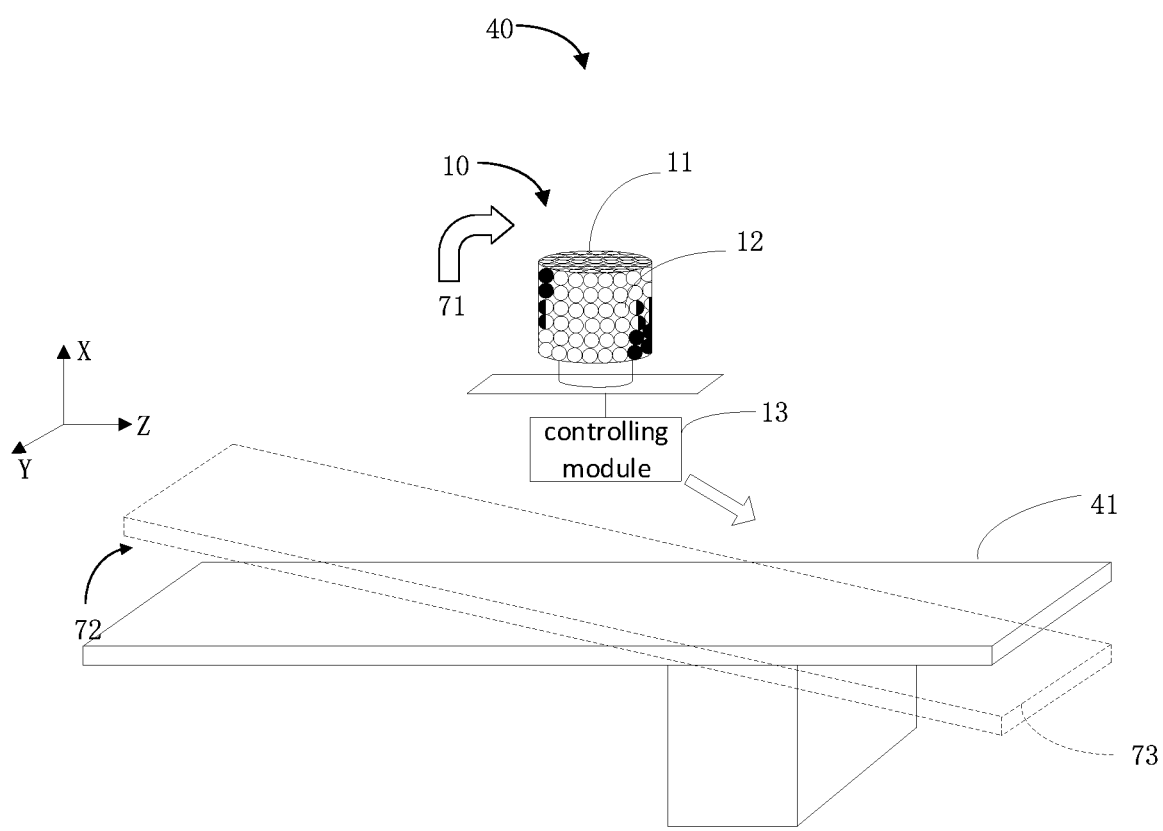
FIG. 7 is a schematic diagram illustrating that a controlling apparatus controls a controlled object to tilt according to an example of the present disclosure.

FIG. 7 is a schematic diagram illustrating that the controlling apparatus 10 controls the controlled object 41 to tilt according to an example of the present disclosure. Tilt of the controlled object 41 may refer to a rotation performed by the controlled object 41 along a direction indicated by the arrow 72 shown in FIG. 7 or a direction opposite to the direction indicated by the arrow 72. As shown in FIG. 7, when the operating body 11 bears an acting force 71, at least one stress sensor 121 of the mechanical sensing apparatus 12 (e.g. the black stress sensors 121 shown in FIG. 7) arranged on a surface of the operating body 11 may sense part of the acting force 71, convert respective part of the acting force 71 sensed into electric signals, and send the electric signals to the controlling module 13. The controlling module 13 may determine a magnitude and a direction of a resultant force of respective parts of the acting force 71 sensed by the at least one stress sensor 121 according to the electric signal and then control the controlled object 41 to tilt along the direction indicated by the arrow 72 shown in FIG. 7. In an example, the controlled object 41 may tilt to a position indicated by a dashed line 73 along the direction indicated by the arrow 72 shown in FIG. 7. Further, the moving speed of the controlled object 41 may be determined according to the magnitude of the resultant force of respective parts of the acting force 71 sensed by the at least one stress sensor 121.

It should be noted that the stress sensors 121 on the side surface 112 of the operating body 11 shown in FIG. 7 are black, which indicates that the stress sensors 121 sense an acting force. In an example, a size of a black area of the stress sensors 121 may be used to represent the magnitude of an acting force sensed by the stress sensors 121. The bigger the black area of the stress sensors 121 is, the greater the acting force sensed by the stress sensors 121 is. Likewise, when the controlled object 41 is to be controlled to tilt along a direction opposite to the direction indicated by the arrow 72 shown in FIG. 7, an acting force along a direction opposite to the acting force 71 may be applied to the operating body 11.

Figure 8:
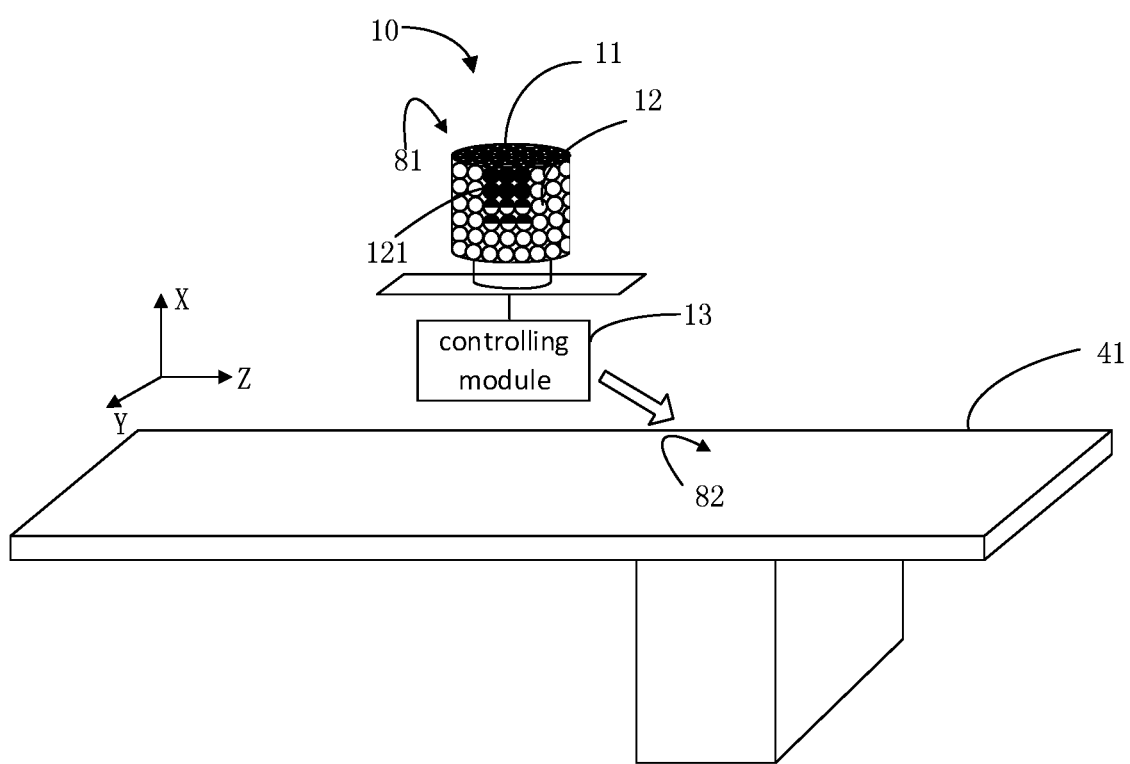
FIG. 8 is a front view illustrating that a controlling apparatus controls a controlled object to sway according to an example of the present disclosure.
Figure 9:
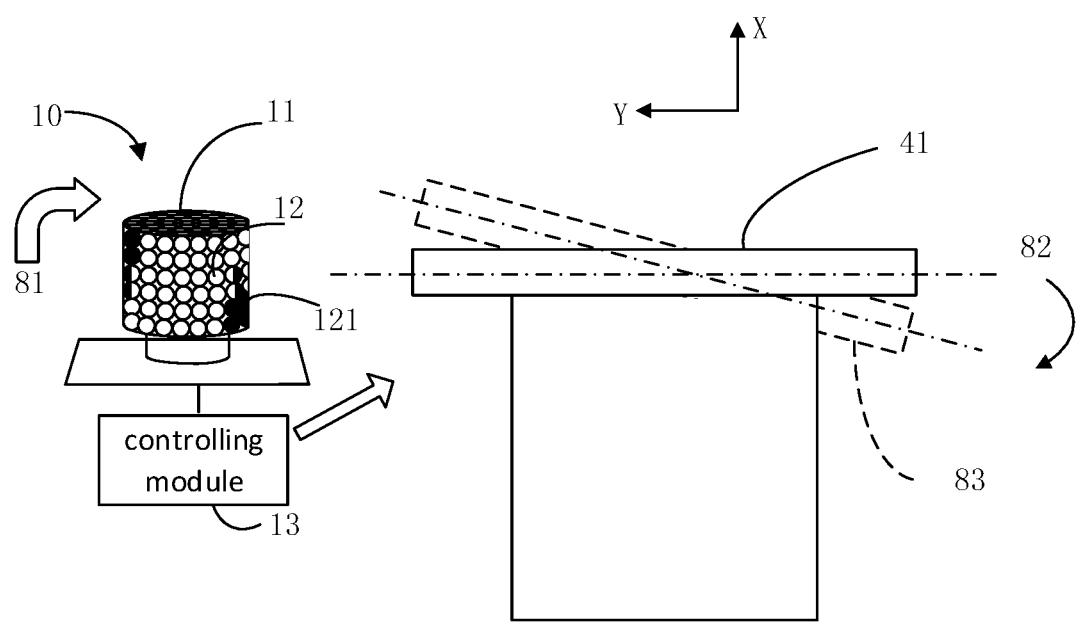
FIG. 9 is a side view illustrating that the controlling apparatus controls a controlled object to sway as shown in FIG. 8.

FIG. 8 is a front view illustrating that the controlling apparatus 10 controls the controlled object 41 to sway according to an example of the present disclosure; and FIG. 9 is a side view illustrating that the controlling apparatus shown in FIG. 8 controls the controlled object 41 to sway. Sway of the controlled object 41 may refer to a rotation performed by the controlled object 41 along the direction indicated by the arrow 82 shown in FIG. 8 and FIG. 9. As shown in FIG. 8 and FIG. 9, when the operating body 11 bears an acting force 81, at least one stress sensor 121 of the mechanical sensing apparatus 12 (e.g. the black stress sensors 121 shown in FIG. 8 and FIG. 9) arranged on a surface of the operating body 11 may sense part of the acting force 81, convert respective part of the acting force 81 into electric signals, and send the electric signals to the controlling module 13. Further, the controlling module 13 may determine a magnitude and a direction of a resultant force of respective parts of the acting force 81 sensed by the at least one stress sensor 121 according to the electric signals and then control the controlled object 41 to sway along the direction indicated by the arrow 82. In an example, the controlled object 41 may sway to a position indicated by a dashed line 83 along the direction indicated by the arrow 82. Furthermore, the moving speed of the controlled object 41 may be determined according to the magnitude of the resultant force of respective parts of the acting force 81 sensed by the at least one stress sensor 121.

It should be noted that the stress sensors 121 on the side surface 112 of the operating body 11 shown in FIG. 8 and FIG. 9 are black, which indicates that the stress sensors 121 sense an acting force. In an example, a size of a black area of the stress sensors 121 may be used to represent the magnitude of an acting force sensed by the stress sensors 121. The bigger the black area of the stress sensors 121 is, the greater the acting force sensed by the stress sensors 121 is.

In addition, when the controlled object 41 is to be controlled to sway along a direction opposite to the direction indicated by the arrow 82, an acting force along a direction opposite to the acting force 81 may be applied to the operating body 11.

Figure 10:
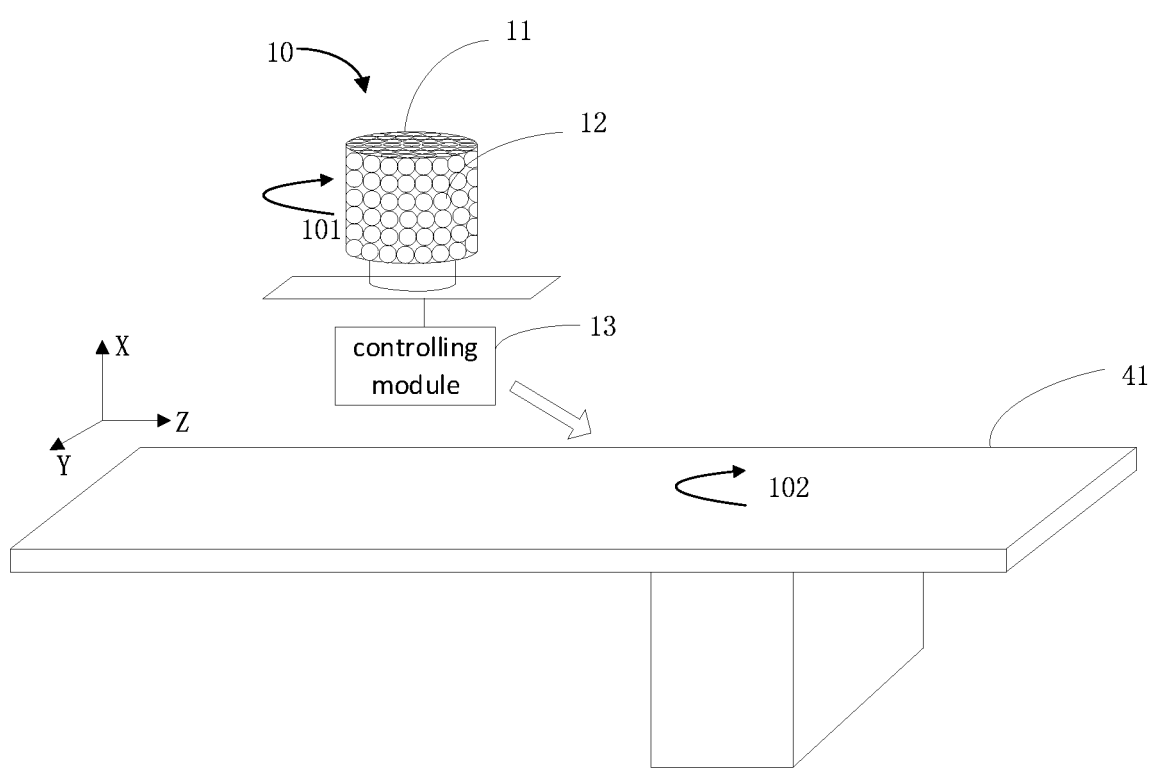
FIG. 10 is a front view illustrating that a controlling apparatus controls a controlled object to rotate according to an example of the present disclosure.
Figure 11:
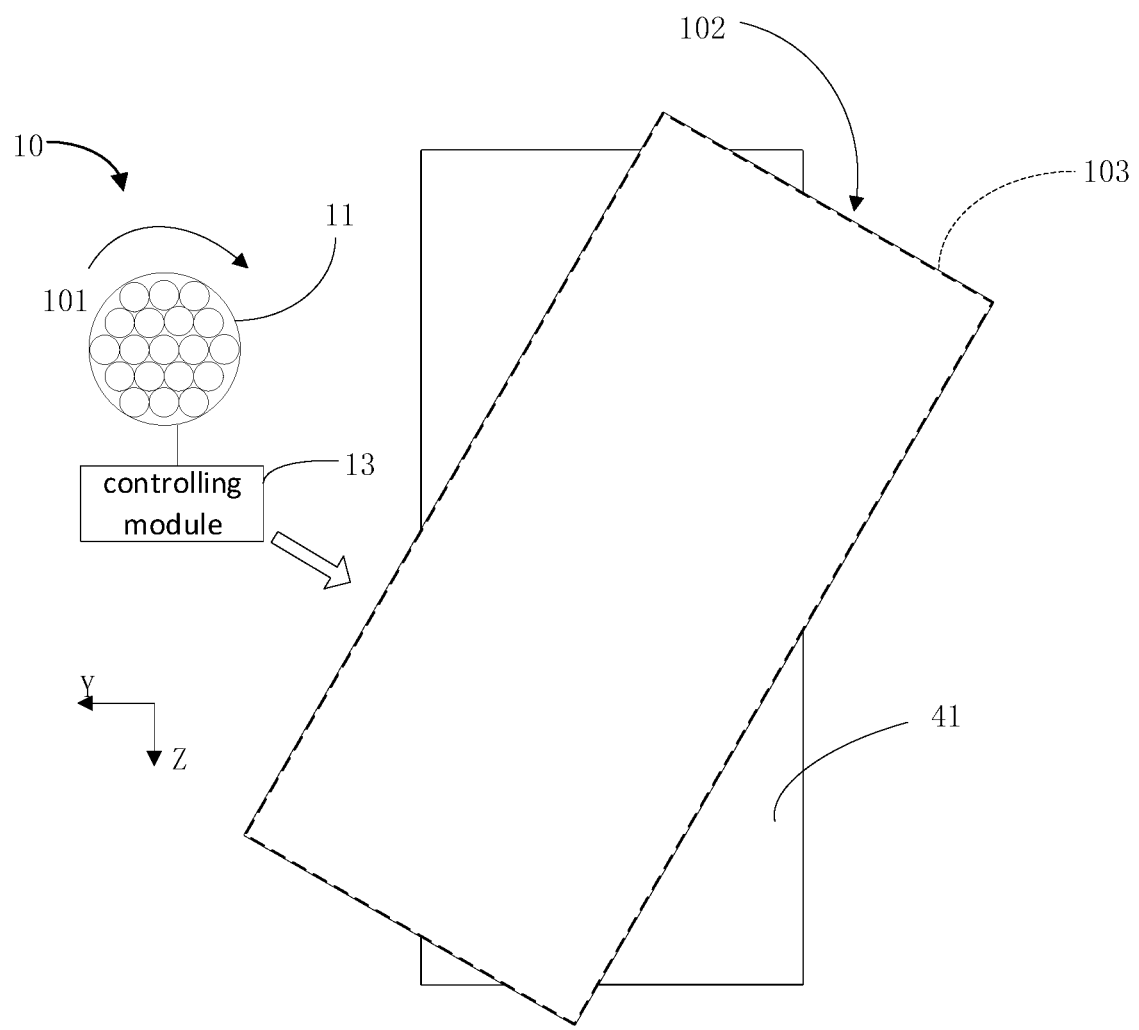
FIG. 11 is a side view illustrating that the controlling apparatus controls a controlled object to rotate as shown in FIG. 10.

FIG. 10 is a front view illustrating that the controlling apparatus 10 controls the controlled object 41 to rotate according to an example of the present disclosure; and FIG. 11 is a side view illustrating that the controlling apparatus shown in FIG. 10 controls the controlled object 41 to rotate. Rotation of the controlled object 41 may refer to a rotation performed by the controlled object 41 along a direction indicated by the arrow 102 shown in FIG. 10 and FIG. 11. As shown in FIG. 10 and FIG. 11, when bearing a rotational acting force 101, the operating body 11 may rotate along a direction indicated by the acting force 101 and generate a rotational electric signal and then send the rotational electric signal to the controlling module 13. The controlling module 13 may control the controlled object 41 to rotate along the direction indicated by the arrow 102 according to the rotational electric signal. In an example, the controlled object 41 may rotate to a position indicated by a dashed line 103 shown in FIG. 10 and FIG. 11 along the direction indicated by the arrow 102.

In addition, when the controlled object 41 is to be controlled to rotate along a direction opposite to the direction indicated by the arrow 102, a rotational acting force along a direction opposite to the acting force 101 may be applied to the operating body 11.

It should be noted that the operating body 11 may generate a rotational electric signal when rotating and the controlling module 13 may control the controlled object 41 to rotate based on the rotational electric signal without converting the acting force into an electric signal by the mechanical sensing apparatus 12.

When controlling the controlled object 41 to move by means of the above-described controlling apparatus 10 provided herein, an operator does not need to learn or memorize the function of an operating button intentionally. Especially in a case of a blind operation, the operator may apply a corresponding acting force to the controlling apparatus 10 to cause a controlled object to move along a direction of a resultant force of the acting force. For example, when a controlled object is be controlled to move along the positive direction of the X-axis, a pushing force along the positive direction of the X-axis is to be applied to the controlling apparatus. Thus, the controlling apparatus may be easily and conveniently operated.

Furthermore, the above-described controlling apparatus provided herein integrates control functions for controlling a controlled object to perform various types of movements into one body. An example of the controlling apparatus only includes one operating body. Thus, an operating space occupied due to arrangement of a plurality of operating buttons and production costs are reduced.

Since method examples substantially correspond to apparatus examples, a reference may be made to part of description of apparatus examples for related parts. The above method may be implemented by the apparatus in the present disclosure and may also be implemented by another apparatus. The method examples and the apparatus examples complement each other.

The foregoing disclosure is merely illustrative of examples of the present disclosure but not intended to limit the present disclosure, and any modifications, equivalent substitutions, adaptations thereof made within the spirit and principles of the disclosure shall be encompassed in the scope of protection of the present disclosure.

The invention claimed is:

1. A controlling apparatus to control a controlled object to move, comprising:
   one operating body configured to bear acting forces, wherein the operating body is cylindrical and rotatable, the controlled object is a scanning bed, and the operating body is disposed beside the scanning bed;
   a mechanical sensing apparatus configured on a surface of the operating body to sense the acting forces and convert the acting forces into electric signals; and
   a controlling module configured to determine a resultant force of the acting forces according to the electric signals and control the controlled object to move along a direction of the resultant force;
   wherein the controlling module comprises:
      a signal amplifier configured to amplify the electric signals from the mechanical sensing apparatus and output amplified electric signals;
      an analog-to-digital converter configured to convert the amplified electric signals from the signal amplifier into digital signals; and
      a controller configured to determine the resultant force of the acting forces according to the digital signals from the analog-to-digital converter and control the controlled object to move along the direction of the resultant force;
   wherein the mechanical sensing apparatus comprises a plurality of stress sensors configured to convert the acting forces at respective positions of the plurality of stress sensors into the electric signals, wherein the plurality of stress sensors are uniformly distributed on the surface of the operating body and contacted with each other; and
   wherein the controlling module receives the electric signals output by the plurality of stress sensors and determines the resultant force of the acting forces according to the electric signals and position information of one or more of the plurality of stress sensors on the surface of the operating body, wherein the one or more of the plurality of stress sensors bear the acting forces.

2. The controlling apparatus according to claim 1, wherein the plurality of stress sensors are distributed on an upper surface, a lower surface, and a side surface of the operating body and contacted with each other.

3. The controlling apparatus according to claim 1, wherein the controlling module is configured to determine a magnitude of the resultant force according to the electric signals and control a moving speed of the controlled object according to the magnitude of the resultant force.

4. The controlling apparatus according to claim 1, wherein the controlling module further comprises:

an anti-jittering module performing an anti-jittering processing on the electric signals and output the electric signals subjected to the anti-jittering processing to the signal amplifier.

5. The controlling apparatus according to claim 1, wherein the controlling module further comprises:
an anti-jittering module performing an anti-jittering processing on the amplified electric signals and output the amplified electric signals subjected to the anti-jittering processing to the analog-to-digital converter.

6. The controlling apparatus according to claim 4, wherein the anti-jittering processing comprises performing filtering and denoising of the electric signals.

7. The controlling apparatus according to claim 1, wherein the operating body is capable of performing a rotation movement; and
the controlling module is capable of controlling the controlled object to rotate according to the rotational movement of the operating body.

8. The controlling apparatus according to claim 1, wherein the controlling module is capable of controlling the controlled object to perform one or more of: a rotation, a tilt, a sway, a translation, an ascent, and a descent.

9. The controlling apparatus according to claim 1, wherein for each of the plurality of stress sensors, the stress sensor comprises:
a substrate;
a resistance grid fixed on the substrate;
a lead connected with an output terminal of the resistance grid; and a cover layer for covering the resistance grid.

10. A medical apparatus, comprising:
a scanning bed, configured to be a controlled object; and
a controlling apparatus configured to control the scanning bed to move,
wherein, the controlling apparatus comprises:
one operating body configured to bear acting forces, wherein the operating body is cylindrical and rotatable, the controlled object is a scanning bed, and the operating body is disposed beside the scanning bed;
a mechanical sensing apparatus arranged on a surface of the operating body to sense the acting forces and convert the acting forces into electric signals; and
a controlling module configured to determine a resultant force of the acting forces according to the electric signals and control the controlled object to move along a direction of the resultant force of the acting forces;
wherein the controlling module comprises:
a signal amplifier configured to amplify the electric signals and output amplified electric signals;
an analog-to-digital converter configured to convert the amplified electric signals into digital signals; and
a controller configured to determine the resultant force of the acting forces according to the digital signals and control the controlled object to move along the direction of the resultant force;
wherein the mechanical sensing apparatus comprises a plurality of stress sensors configured to convert the acting forces at respective positions of the plurality of stress sensors into the electric signals, wherein the plurality of stress sensors are uniformly distributed on the surface of the operating body and contacted with each other; and
wherein the controlling module receives the electric signals output by the plurality of stress sensors and determines the resultant force of the acting forces according to the electric signals and position information of one or more of the plurality of stress sensors on the surface of the operating body, wherein the one or more of the plurality of stress sensors bear the acting forces.

11. The medical apparatus according to claim 10, wherein the plurality of stress sensors are distributed on an upper surface, a lower surface, and a side surface of the operating body and contacted with each other.

12. The medical apparatus according to claim 10, wherein the controlling module is configured to determine a magnitude of the resultant force according to the electric signals and control a moving speed of the controlled object according to the magnitude of the resultant force.

13. The medical apparatus according to claim 10, wherein the controlling module further comprises:
an anti-jittering module performing an anti-jittering processing on the electric signals and output the electric signals subjected to the anti-jittering processing to the signal amplifier.

14. The medical apparatus according to claim 10, wherein the controlling module further comprises:
an anti-jittering module performing an anti-jittering processing on the amplified electric signals and output the amplified electric signals subjected to the anti-jittering processing to the analog-to-digital converter.

15. The medical apparatus according to claim 13, wherein the anti-jittering processing comprises performing filtering and denoising of the electric signals.

16. The medical apparatus according to claim 10, wherein for each of the plurality of stress sensors, the stress sensor comprises:
a substrate;
a resistance grid fixed on the substrate;
a lead connected with an output terminal of the resistance grid; and a cover layer for covering the resistance grid.

* * * * *